US006607501B2

United States Patent
Gorsuch

(10) Patent No.: US 6,607,501 B2
(45) Date of Patent: Aug. 19, 2003

(54) PROCESS AND APPARATUS FOR UTILIZATION OF IN VIVO EXTRACTED PLASMA WITH TISSUE ENGINEERING DEVICES, BIOREACTORS, ARTIFICIAL ORGANS, AND CELL THERAPY APPLICATIONS

(75) Inventor: Reynolds G. Gorsuch, 1119 State La., Yountville, CA (US) 94599

(73) Assignees: Reynolds G. Gorsuch, Napa, CA (US); Transvivo, Inc., Napa, CA (US)

( * ) Notice: Subject to any disclaimer, the term of this patent is extended or adjusted under 35 U.S.C. 154(b) by 67 days.

(21) Appl. No.: 09/858,029

(22) Filed: May 14, 2001

(65) Prior Publication Data

US 2002/0188240 A1 Dec. 12, 2002

(51) Int. Cl.[7] .............................................. A61M 37/00
(52) U.S. Cl. ..................... 604/5.01; 604/6.04; 604/6.09
(58) Field of Search .............................. 604/4.01, 5.01, 604/5.02, 5.03, 5.04, 6.01, 6.02, 6.03, 6.04, 6.05, 6.06, 6.07, 6.08, 6.09, 6.1, 6.11, 6.12, 6.13, 6.14, 6.65, 6.16, 7, 8, 9, 10

(56) References Cited

U.S. PATENT DOCUMENTS

| 4,832,034 A | | 5/1989 | Pizziconi et al. ........... 128/632 |
|---|---|---|---|
| 4,950,224 A | * | 8/1990 | Gorsuch et al. ........... 604/6.04 |
| 5,145,583 A | | 9/1992 | Angleraud et al. .......... 210/646 |
| 5,151,082 A | | 9/1992 | Gorsuch et al. ............... 604/4 |
| 5,224,926 A | | 7/1993 | Gorsuch et al. ............... 604/4 |
| 5,735,809 A | | 4/1998 | Gorsuch ....................... 604/4 |
| 5,955,353 A | | 9/1999 | Amiot ......................... 435/297 |
| 5,968,004 A | | 10/1999 | Gorsuch ....................... 604/4 |
| 5,989,913 A | * | 11/1999 | Anderson et al. ......... 435/286.7 |
| 6,008,049 A | * | 12/1999 | Naughton et al. ........... 435/1.1 |
| 6,080,581 A | * | 6/2000 | Anderson et al. ........... 435/394 |
| 6,218,182 B1 | * | 4/2001 | Naughton et al. ........... 435/1.1 |

FOREIGN PATENT DOCUMENTS

EP          0 801 973 A1    10/1997

* cited by examiner

Primary Examiner—Edward K. Look
Assistant Examiner—John K Fristoe, Jr.
(74) Attorney, Agent, or Firm—Knobbe, Martens, Olson & Bear, LLP

(57) ABSTRACT

The present invention is directed to a method of treating cells, tissues or organs using in vivo plasma separation by implanting a plasma separation filter device within a blood vessel of a patient, or allogenic, or xenogenic donor, continuously separating blood plasma from whole blood in vivo, directing the plasma from the plasma separation filter device to a bioreactor, and exposing the plasma to cells, tissue or an organ within the bioreactor utilizing immune separation membranes where necessary.

32 Claims, 4 Drawing Sheets

Generic Bioreactor and Autologous Hybrid artificial Organ System

PROCESS AND APPARATUS FOR UTILIZATION OF IN VIVO EXTRACTED PLASMA WITH TISSUE ENGINEERING DEVICES, BIOREACTORS, ARTIFICIAL ORGANS, AND CELL THERAPY APPLICATIONS

BACKGROUND OF THE INVENTION

The present invention relates to in vivo plasmapheresis as described in U.S. Pat. Nos. 4,950,224 and 5,735,809. More particularly, the present invention relates to methods and apparatus for the continuous utilization and/or treatment of the in vivo extracted plasma in ex vivo or implanted devices, fermentors, bioreactors, and other mechanisms developed and used in the fields of tissue engineering, cellular therapy, artificial organs, and the like.

Many diseases and disorders result from disruption of cellular function or destruction of tissues and of the body. Physicians treat tissue loss or organ failure with drug therapy, organ transplantation, surgical reconstruction, or mechanical devices. However, drug therapy is usually expensive, not always effective, and many patients suffer from serious side effects, suitable transplantable tissue and organs are in short supply, often with immune rejection, and current mechanical devices cannot perform all the functions of a single organ. Thus, there is a need for improved treatments for these diseases and disorders.

All of the aforesaid fields of science use bioreactors and other such mechanisms used in biotechnology as well as drugs or chemical processes used in plasma protein manipulations and the subsequent return of the modified plasma to the body to treat, modify, or reconstitute specific physiological functions. These applications are emerging sciences that use in vivo and ex vivo cell cultures and cell-secreted protein products to reconstitute body parts, tissues, and organs, in functional artificial organs (such as the pancreas and liver), and in specialized fermenters, and continuous cultures to create or modify immune system components and constructs for treatment of specific disease states. Such devices and bioreactors are also useful for the expansion of cell cultures and their subsequent harvesting and re-transplantation in patients whose immune system and stem cell population has been decimated by chemical and radiation therapy. Such devices and bioreactors are also useful to act as the access mechanism and transport vehicle for monitoring and effecting drug or gene therapy that may be difficult or cannot be performed in vivo because of the toxicity or trauma of the process. In the case of artificial organs, autologous, xenogenic, and allogenic cells and tissues as well as substitute materials and mechanisms may be used to perform the functions of the organ implanted or ex vivo and remote from the physiological site of the original organ in an artificial construct. These ex vivo devices can also be used to isolate, separate, and harvest and/or modify specific human immune system proteins, that reside in the plasma, by means of series cascade filtration, or by means of selective ligand attachments to hollow fibers or other substrates in the plasma flow stream.

Cell culture bioreactors are systems which have one or more of the following purposes: (a) the expansion (replication) of specific human cells and/or tissue complexes to be used for therapeutic re-implantation, (b) the expression (production) of cells and/or cellular products (antibodies, cytokines, proteins, immune system complexes, etc.) to be used in the therapy of specific disease states, (c) the utilization of such cellular cultures and cell populations which mimic the performance of in vivo tissue to perform in substitution or in supportive augmentation of the functions of organs (i.e., pancreas, liver) and other specialized tissues (i.e., cartilage), and (d) to act as vehicles for the modification of cells by gene therapy techniques. In the case of artificial organs, such cellular activity may be augmented, supported, controlled, or replaced by alternate electromechanical or chemical system constructs providing specialized functions such as respiration, separation, filtration, sensor transduction, signal conditioning, computation, and system control effectors.

An example of both (a) and (b) purposes occurs in cancer therapy where hyper-intensive chemotherapy is used for efficient destruction of the oncocellular tissue and which also destroys the bone marrow and circulating stem cells responsible for the genesis of the human immune system. Treatment protocol in this case is to stimulate and harvest bone marrow and/or peripheral circulating stem cells and place them in cryo-storage, or a bioreactor, prior to and pending completion of the chemotherapy. The harvested stem cells are re-implanted, and in time regenerate the immune system and re-populate the patient's stem cell structure.

A bioreactor may be of any class, size or have any one or number of desired features, depending on the product to be achieved. Different types of bioreactors include tank bioreactors, immobilized cell bioreactors, hollow fiber and membrane bioreactors as well as digesters. There are three classes of immobilized bioreactors, which allow cells to be grown: membrane bioreactors, filter or mesh bioreactors, and carrier particle systems. Membrane bioreactors grow the cells on or behind a permeable membrane, allowing the nutrients to leave the cell, while preventing the cells from escaping. Filter or mesh bioreactors grow the cells on an open mesh of an inert material, allowing the culture medium to flow past, while preventing the cells from escaping. Carrier particle systems grow the cells on something very small, such as small nylon or gelatin beads. The bioreactor can be a fluidized bed or a solid bed. Other types of bioreactors include pond reactors and tower fermentors.

Different bioreactors utilize different components for mixing the contents including the use of stirring paddles, turbines, deep jet fermentors, gas inflow, etc. Bioreactor control may be achieved by any desired purpose, including biomass sensors and real-time off-line sensors. Bioreactors may also be classified according to how they keep contaminants excluded.

Presently, all apparatus, systems and methods utilize blood or plasma and/or serum media separated from blood of the patient of an allogenic or xenogenic donor by ex vivo means such as centrifugation or ultrafiltration. Blood contains erythrocytes, platelets or other large molecular weight blood components which will coagulate or clot in the ex vivo components causing disruption if not inoperability of the systems. Centrifugation or ultrafiltration requires purchase and operation of additional apparatus, thereby substantially increasing the cost of the procedure and are bulky and thus immobilizes the patient. Centrifugation also requires a significant amount of blood, placing an unacceptable burden on the patient or allogenic donor. Moreover, the processing of whole blood substantially increases the incidence of infection or contamination of the blood cells, and ultimately the patient as well as the incidence of damage to the red and white blood cells.

Some proposed bioreactor systems utilize whole blood removed from the patient or donor and separate the plasma into the blood from the blood cells ex vivo. Such plasmapheresis systems do not obviate the disadvantages discussed above since whole blood still must be removed from the source and filtered to separate the plasma to be directed to the bioreactor. It is to the elimination of the aforesaid disadvantages that the present invention is directed.

SUMMARY OF THE INVENTION

The present invention is directed to a method of continuously providing cell culture media to cells, tissues or organ constructs in bioreactors, tissue engineering devices, artificial organs, and other cell culture devices using in vivo plasma separation by implanting a plasma separation filter device within a blood vessel of a patient, or donor separating blood plasma from whole blood in vivo, directing the plasma from the plasma separation filter device to a bioreactor or other cell culture device, and exposing the plasma to cells, tissue or an organ within the bioreactor or other cell culture device directly or indirectly through a membrane immune system barrier. Expressed or replicated cells, tissue segments, other cell culture products are recovered or harvested and may be directed to a selected delivery system where cell products, cells or tissues may be directed to specific patient sites or implanted in the patient. Alternatively, the culture product may be returned to the patient's blood. The spent cell culture media (plasma) may be discarded or returned to the patient or donor blood where it can be revitalized and reconstituted by the donors organs (i.e. kidneys or liver) for reuse in the bioreactor device on a continuous basis. The invention includes apparatus for carrying out the aforesaid method.

DETAILED DESCRIPTION OF THE PREFERRED EMBODIMENTS

The present invention is directed to a method and apparatus for using plasma derived from in vivo separation of blood directly as the culture media in bioreactors and/or as the source of plasma proteins used in the fields of tissue engineering, cellular therapy and artificial organs.

A method and apparatus for treating cells, tissues, or organs using in vivo plasma separation is provided. A plasma separation filter device, implanted within a blood vessel of a patient, separates plasma from whole blood and directs the plasma to a bioreactor. The plasma is exposed to the cells, tissue or an organ contained within the bioreactor. The cellular product and/or cells, tissue, and organs are returned to the patient's body. Spent plasma from the bioreactor may also be returned to the patient's body for reconstitution by the patients organs and reused.

Figure 1:
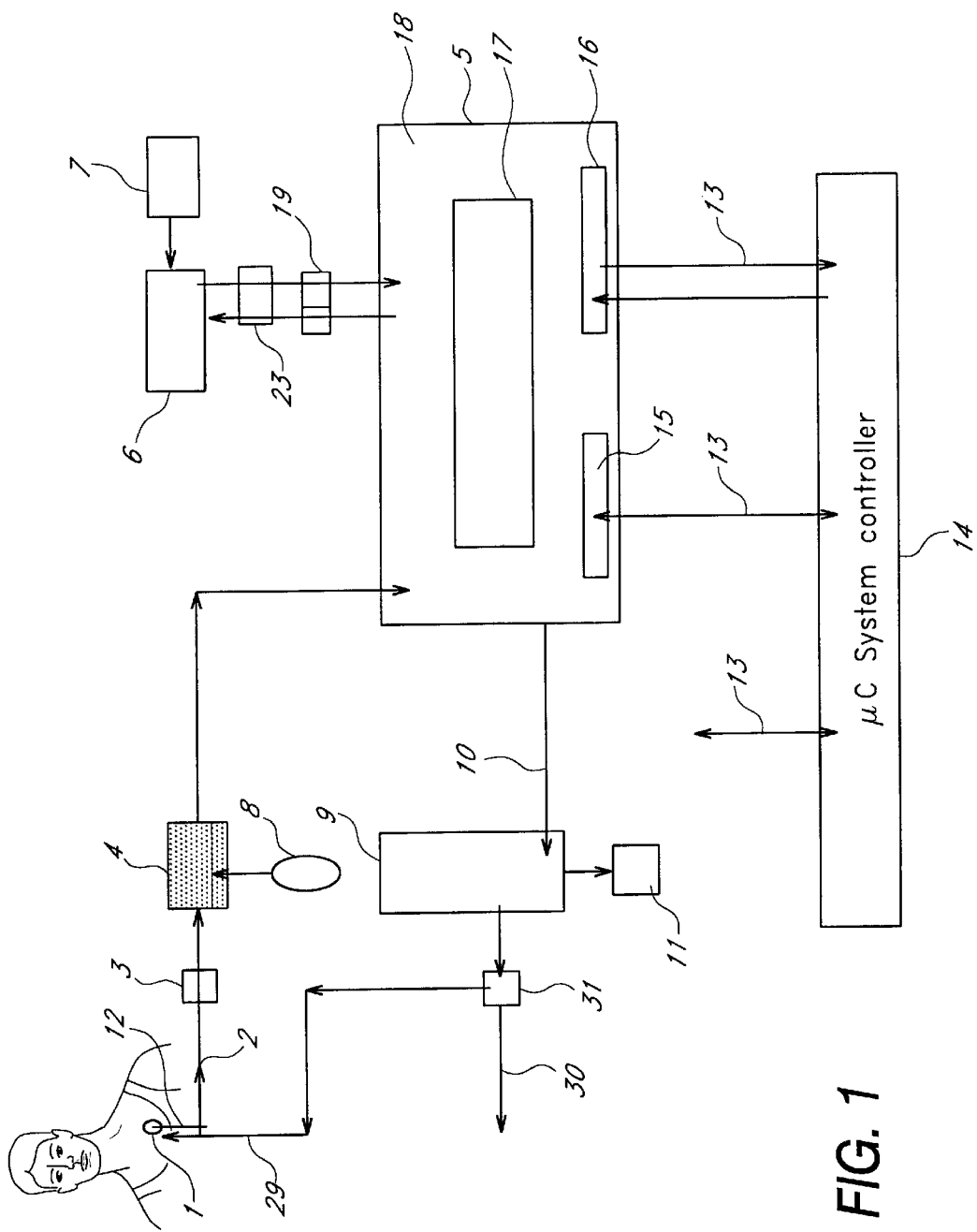
FIG. 1 schematically illustrates an apparatus of the invention used for an autologous hybrid artificial organ application where both the cultured cells and the plasma source are of the patient.
Figure 3:
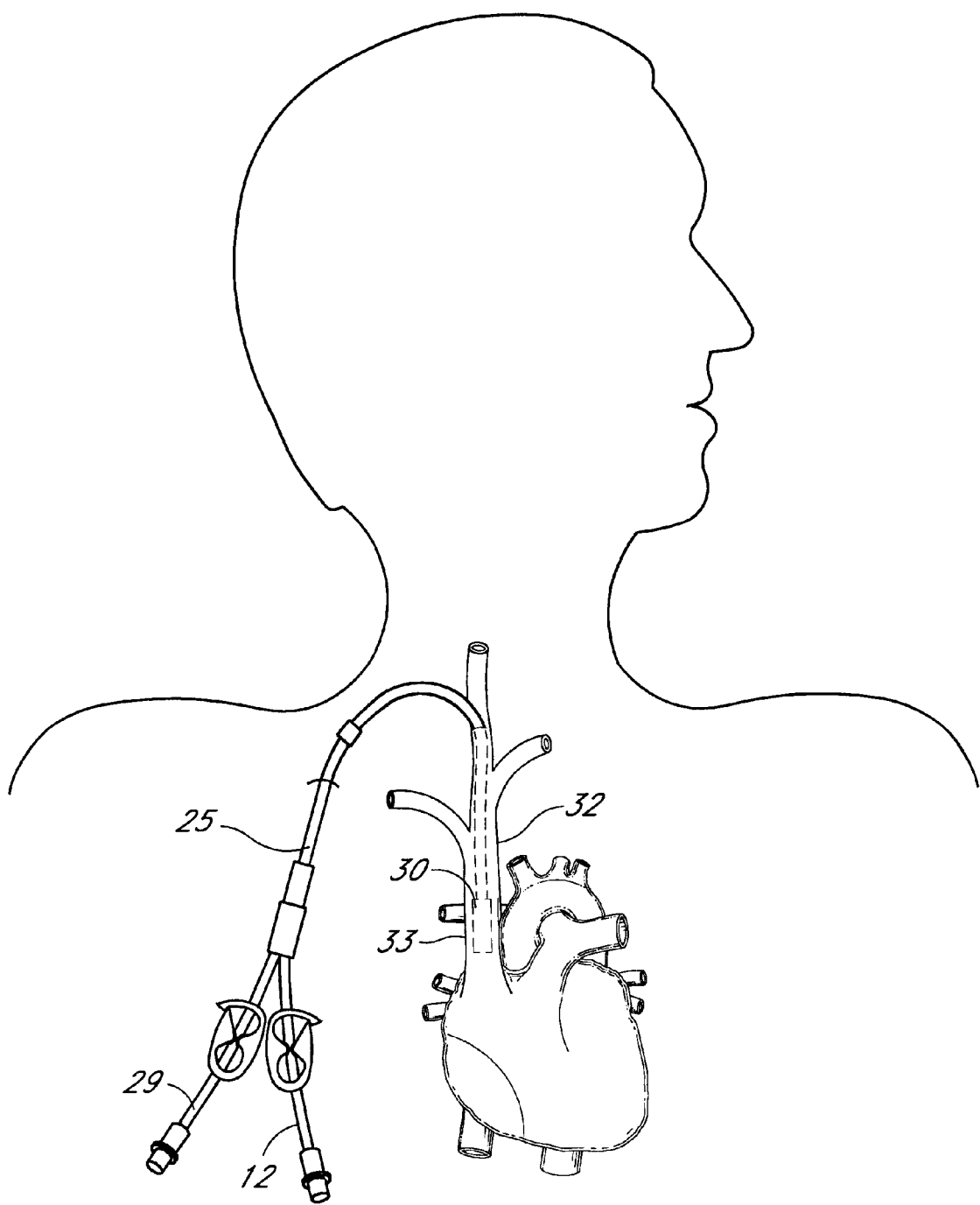
FIG. 3 schematically illustrates one embodiment of the implanted filter and catheter by which plasma is separated from blood in vivo and routed ex vivo for treatment and/or utilization.

FIG. 1 illustrates a system according to the present invention utilizing autologous plasma and autologous cells and incorporating a generic bioreactor fed by plasma derived from the in vivo plasma separation assembly 1 which includes a filter device and a dual lumen catheter as shown in FIG. 3 and described hereinafter. In this embodiment the in vivo separated plasma is directly exposed to cells, tissue or organ in the bioreactor. The bioreactor and features for any given application will be selected depending on the requirement and purpose desired. Plasma and cell products may be returned to the patient via a separate catheter or delivery system to the capillary bed of a specifically targeted tissue structure or organ.

In the apparatus shown autologous plasma from the plasma separation unit 1 is transported to the bioreactor 5 via conduit 2 and delivered to the seeded cell culture bed 17 via a flow control unit 3. The seeded cell culture unit substrate may be any substrate used in the industry for immobilization of the cells. Examples include collagen matrix, collagen beads, glass beads, magnetized beads, hollow fiber membranes (intra and extra capillary space), flat sheet membranes, spiral wound and stacked sheet membranes, and shaped bioresorbable polymer matrices.

The culture media (plasma) 18 surrounds the cell culture bed and may flow on, around and/or through the bed in order to perfuse all cells in the culture. A fluid circulator may be used to ensure proper mixing of the culture media within the bioreactor, e.g., an impeller, stirrer, turbine, deep jet fermentor, pump, etc. While the primary culture media may be the autologous plasma, any particular cell application may require supplementation with such components as horse or other sera, nutrients, growth factors, cytokines, and drugs which are delivered to the culture media 18 chamber within the bioreactor via flow controller 3 with mixing being assured by the fluid circulator. Other bioreactor parameters such as temperature, pressure, etc., may be controlled by environmental control device 15.

Cell culture respiration is provided by the tonometered plasma product of a hollow fiber gas exchange unit 4 with gas ($O_2$,$N_2$) supplied by supply source 8, and controlled by the system controller 14 in response to pH, and $O_2$ sensor readings in the sensor array 16. The sensor array may contain any number of different sensors that may be required for the application in use., i.e., osmolality, glucose, etc. Suitable sensors include biomass sensors and real time off-line sensors. The system controller 14 monitors and controls flow controllers 3 and 31, bioreactor environmental control device 15 and sensor array 16 via input/output control signals 13.

While the culture media may be constantly replaced by incoming plasma and augmented by selected supplements from a supplement source 7, a buildup of toxic elements and metabolites may occur. The optimum level of these substances are maintained by a modulation media distributor 6 controlled by the flow controller 23 unit which may modulate the composition, and the osmolality of the culture media 18 by injection, dialysis, diffusion and/or ultrafiltration. Composition of the resulting modulated culture media is determined by analysis of samples taken through sample port 19 and/or the output of sensor array 16.

The clinical product of the bioreactor comprises cell colonies or differentiated tissue colonies, and cell products, proteins, antibodies, cytokines, etc. Cell and tissue colonies can be harvested from the bioreactor periodically without damage of the bioreactor by temporary shutdown of the reactor and extraction of the tissue or colony. They are then implanted into the patient by infusion or surgical means, or inserted into a secondary reactor for further expansion, or frozen and placed in storage to summate to a suitable critical mass. The culture product of the bioreactor comprising cell products, proteins, antibodies, etc. is continuously extracted from the bioreactor via the return plasma conduit 10. The culture product is further refined by the culture product refinement apparatus components 9, the outlet flow of which is controlled by flow control unit 31.

The culture media 18 has been modified by the previously described systems to ensure optimal cell growth conditions and cell product output. However, the plasma and the cell product along with metabolites and other components are all mixed in with the media and most likely will not represent an optimum and/or desirable plasma mix for return to the patient in compliance with the demands of the therapy application involved. For example, it may be desirable to remove LDL cholesterol, or other lipoproteins by cascade filtration or absorption column, IgG Fu components by Protein A affinity column, specific components with cluster of differentiation selection by electromagnetic means, and other suitable separation mechanisms known in the art before delivery of the culture product to the patient via catheter 29 or by a delivery device 30. Waste products undesirable for delivery to the patient may be collected from the culture product refinement apparatus 9 into an appropriate container 11 for disposal.

The specific type, components and features of the bioreactor to which the in vivo separated plasma is directed according to the invention is not a part of the present invention, and will be selected by those skilled in the art.

Figure 2:
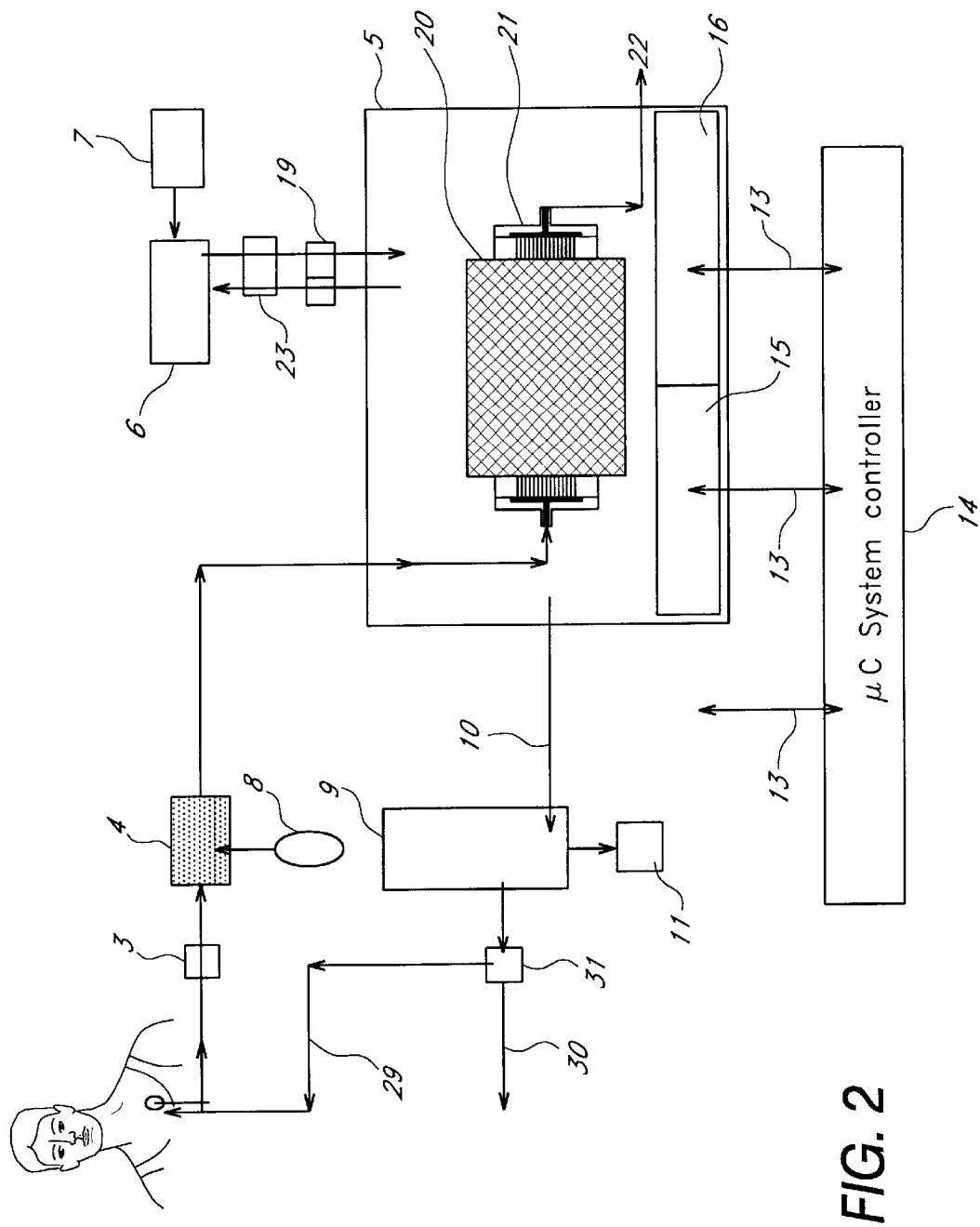
FIG. 2 schematically illustrates a system application used for allogenic or xenogenic bioreactor and hybrid artificial organ applications where either the plasma source or the cultured cells are allogenic or xenogenic.

It is most desirable to use a patient's own cells to repair a defect, thereby avoiding problems with immune rejection and contamination. Where autologous media cannot be used for clinical or other reasons and allogenic or xenogenic plasma and/or allogenic or xempgenic cell must be used in the system immunoisolation between the delivered plasma and the cells used may be provided by the use of hollow fiber or sheet membrane bioreactor constructs as illustrated in FIG. 2. For example, an allogenic or xenogenic cell culture bed 20 may be incorporated and/or a hollow fiber membrane assembly 21 with plasma return conduit 22 used. Again, such components are known to those skilled in the art. Other system components are like those described in FIG. 2.

Preferably, the bioreactor is extracorporeal (ex vivo). Extracorporeal systems, which can be used when a patient's own organ is failing offer several advantages: (1) better control of the medium surrounding the cell system (for example, the ability to achieve improved transport of oxygen, nutrients, and wastes); (2) better control of the timing and duration of use; and (3) a decreased chance of immune rejection because the patient's white cells can be separated from hepatocytes by plasmapheresis.

FIG. 3 illustrates the apparatus by which plasma is separated from blood in vivo and routed ex vivo for treatment and/or utilization as described therein. A plasma separation assembly includes a filter device 30 percutaneously implanted in the superior vena cava 33 via the interior jugular vein 32. Alternatively the filter device could be unplanted in the inferior vena cava via a femoral vein. The filter device 30 installed on the proximal end of a dual lumen catheter 25 extracts plasma from the blood flowing in the vein and conducts it via the outflow lumen of the catheter 12 ex vivo for utilization. In a preferred embodiment, the filter element of the plasma separation assembly comprises a hollow fiber and/or sheet membrane having a pore size capable of separating blood plasma and selected components from whole blood. The so-extracted plasma after utilization is returned to the body vasculature via the return lumen 29 of the catheter maintaining a continuous source of fresh plasma for the bioreactor and providing a means of reconstituting the utilized plasma by the donors organs. Preferably, the plasma source is the patient. Where autologous media is not available, the device may be used to extract allogenic or xenogenic media and the cell culture product and/or tissue constructs introduced to the patient by separate means.

A filter device such as disclosed in U.S. Pat. Nos. 4,950, 224, 5,224,926, 5,735,809 and 5,968,004 may be used. Such devices comprise elongated hollow fibers and various filter assembly designs incorporating the hollow fibers which may be used in the apparatus for carrying out the present invention. A preferred fiber membrane used in the filter device 30 is disclosed in U.S. patent application Ser. No. 09/549,131 filed Apr. 13, 2000, (TRANSVI.007A) the description of which is incorporated herein by reference. The wall structure of the fiber from the outer surface to the lumen is a continuum with non-linear pore and void distribution. The resulting structure is a continuous change in mass density between the outer surface of the fiber and the inner lumen surface. Such a membrane has a plurality of zones between the inner and outer wall surfaces, each zone having a different mass density than the mass density of an adjacent zone. The membrane fiber wall may have two, three or four or more mass density zones with a lower mass density zone at the inner wall surface and a higher mass density zone at the outer wall surface. Each zone is characterized by a different average nominal pore size, with a lower mass density zone having a nominal average pore size of between about 1 $\mu$m and about 60 $\mu$m and a higher mass density zone having a nominal average pore diameter of between about 0.3 $\mu$m and about 1 $\mu$m. A preferred membrane has the capability of extracting at least 0.75 (ml/min)/(cm×mm Hg) at transmembrane pressures of between about 5 mm and about 20 mm Hg. Preferred fibers have a sieving coefficient cutoff of between $2 \times 10^4$ and $4 \times 10^6$ Daltons.

Figure 4:
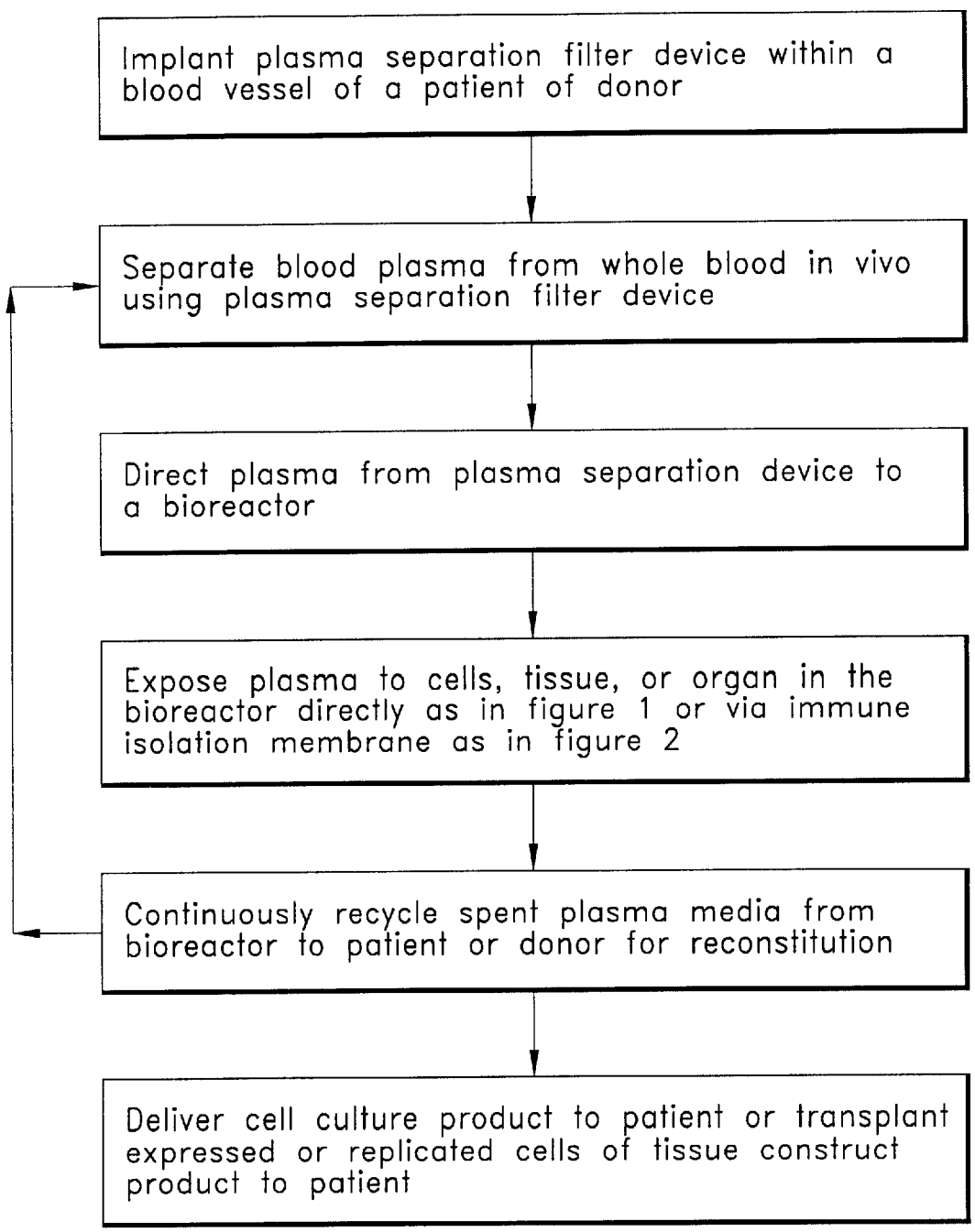
FIG. 4 schematically illustrates sequential, general steps for treating cells, tissue, or organs within a bioreactor, delivery of the generated and product, and reconstitution of the plasma media.

FIG. 4 shows sequential steps for exposing extracted plasma to cells, tissue, or an organ within a bioreactor. Preferably, a plasma separation device is implanted within a blood vessel of a patient, separating blood plasma from whole blood in vivo. In general, the device is percutaneously installed in the superior vena cava via the interior jugular vein, or alternatively in the inferior vena cava via a femoral vein. The plasma, which is separated from the whole blood via the separation element, is directed from the plasma separation filter device to a bioreactor, exposing cells, tissue, or an organ within the bioreactor to the plasma. A plasma culture product from the bioreactor is recovered and may be directed to a selected cellular delivery system, or the culture product may be returned to the patient's blood.

Preferred bioreactors include but are not limited to cell culture bioreactors and artificial organs. Cell culture bioreactors can be simple limited purpose, limited life, implanted in vivo capsules placed in strategic application sites, or extremely complex ex vivo continuous perfusion systems with multiple media, metabolic, and respiration support and control systems. Artificial organs, on the other hand, can be simple mechanical systems, as in the case of the artificial kidney where the toxins are removed by diffusion (dialysis) and the excess body fluids are removed by ultrafiltration as described in U.S. Pat. No. 5,151,082, or they may be hybrid devices utilizing both mechanical systems and bioreactors as in the case of an artificial pancreas and an artificial liver.

The use of in vivo separated plasma in a system described herein according to the invention has several major advantages when used in conjunction with cell culture bioreactors and/or hybrid systems which support the patient involved. The autologous plasma used will not cause a "graft vs. host" reaction from the seeded patient autologous cells in the bioreactor culture bed because they are both derived from the same individual and thus will not trigger an immune response. The autologous plasma used as culture media will contain antibodies, immune complex proteins, cytokines, growth factors, etc. which will reflect the general immune complex conditioning which is specific to the patient's reactive requirements. However where such immune system or other plasma components may need to be modified, extracted, modulated, or manipulated prior to use in the bioreactor or construct in order to effect specific therapies, a system for that purpose can be placed in series with the extracted plasma flow from the patient to the bioreactor providing those functions continuously.

The system exposes the extracted plasma to cells, tissues, or an organ within the bioreactor. The plasma provided and returned to the patient will provide a transport system to deliver the expressed cell product to the patient and to the appropriate patient cells and tissues for therapy either through the venous return system or directly to the capillary bed of specialized tissues through means of a separate catheter. The plasma provided acts as the cell culture media, and will also contain the majority of the nutritional components required by the bioreactor having been generated by the patient's nutritional and digestive systems and in most cases requiring only supplements.

The cellular biomass in the bioreactor is but a minor fraction of the body mass of the patient. Consequently, the flow rate of the plasma media through the bioreactor will be substantially less than required by such systems as the kidney dialysis system described in the U.S. Pat. No. 4,950, 224 patent. It is estimated that sufficient plasma for the bioreactor could be supplied by a much smaller plasmapheresis catheter in a peripheral artery or vein, which would simplify its placement and ultimate removal as well as argue to the feasibility of an ambulatory system in a number of cases. Based on the cell expansion rates reported in continuous perfusion bioreactors it is feasible to periodically harvest the cultured cells for implantation simultaneously with the generation of cell product therapy proteins, thus ultimately reducing the requirement for the procedure without interrupting the therapy.

The in vivo plasma provided would not contain erythrocytes, platelets, or other large molecular weight blood components, and thus would not coagulate or clot in the in vitro devices rendering them inoperable, as is the case in systems utilizing whole blood. Based on the principals of pharmacokinetics, continuous treatment systems as herein postulated are more effective, efficient, and produce better outcomes sooner than off-line, batch process techniques that have been reported in the literature in that effective concentrations of active elements could be continuously maintained at an optimum level. The in vivo plasma provided would be the primary exudate extracted from the vasculature and would not be whole blood as currently practiced which, if used unfiltered as media, would and does clot in the bioreactor or if separated ex vivo by a centrifuge by membrane filtration would constitute an extra inconvenient and costly step in the process.

Utilization of the plasmapheresis-bioreactor system of the present invention achieves two important results. Such use expands the harvested stem cells to ensure that sufficient cells would be available to complete the therapy and/or multiple sessions of the therapy, thereby shortening the overall treatment regime. It also permits the delivery of immune system complexes to the patient immediately after therapy and prior to the reconstitution of the patient's stem cell population, thus shortening the patient's recovery time and hospital stay in sterile isolation pending the recovery of his or her immune system. Further, through the use of growth factors, or growth inhibiting drugs, stem cells or colony forming units (CFU's) can be controlled such that only specific functional cells can be produced as required. The advantages include substantial reduction in economic burden and infection risk.

Cell culture of lymphoid stem cells may be used to expand B lymphocytes, T lymphocytes, plasma cells, and helper T cells. Selective exposure of this culture to specific antigens in relative ex vivo isolation may produce appropriate antibodies and lymphokines, and excite the classical pathway of complement activation, acting as a form of vaccine which could be titrated into the patient's bloodstream on an appropriate schedule to possibly upgrade the patient immune response to the secondary exposure efficiency response curve. The bioreactor system of the invention may be used to co-culture hepatocytes and Kupfer cells to act as a supportive adjunct to a failing liver, as reported in the literature, to extend life while a transplant is being sought. They system could also be used effectively as an artificial pancreas, using the signal from a glucose sensor for the proportional activation of insulin injection into the plasma or to regulate the plasma flow across transgenetic or autologous cultured islet cells producing the needed insulin.

EXAMPLES

The system exposes the extracted plasma to a patient's own cells, tissue, or an organ within a bioreactor. In a preferred embodiment, stem cells from the patient are used in the bioreactor to grow and reproduce more cells or tissue to turn into useful tissue or to return those to the body. Alternatively, stem cells can be obtained from an another source, where the source is another person or a non-human animal.

A definition of a stem cell is provided by Potten and Loeffler (Development, 110:1001, 1990), who have defined stem cells as "undifferentiated cells capable of a) proliferation, b) self-maintenance, c) the production of a large number of differentiated functional progeny, d) regenerating the tissue after injury, and e) a flexibility in the use of these options."

Stem cells have the ability to divide for indefinite periods in culture and to give rise to specialized cells. There are three types of stem cells: pluripotent, totipotent, and multipotent. Pluripotent cells are capable of giving rise to most tissues of an organism. Totipotent stem cells have unlimited capability. For example, totipotent cells have the capacity to specialize into extraembryonic membranes and tissues, the embryo, and all postembryonic tissues and organs. Multipotent stem cells are pluripotent stem cells which undergo further specialization which give rise to cells that have a particular function.

Stimulation of stem cells, may become a source of replacement cells and tissue to treat a myriad of diseases, conditions, and disabilities. Table 1 shows some possible uses of tissue derived from stem cells to treat disease.

Alternatively, tissue or organs from the patient may be used in the bioreactor to regenerate or reproduce new tissue or to produce the desired culture product.

TABLE 1

Possible Uses of Tissue Derived From Stem Cells to Treat Disease

| Cell type | Target Disease |
| --- | --- |
| Neural (nerve) cells | Stroke, Parkinson's disease, Alzheimer's disease, spinal cord injury, multiple sclerosis |
| Heart muscle cells | Heart attacks, congestive heart failure |
| Insulin-producing cells | Diabetes |
| Cartilage cells | Osteoarthritis |
| Blood cells | Cancer, immunodeficiencies, inherited blood diseases, leukemia |
| Liver cells | Hepatitis, cirrhosis |
| Skin cells | Burns, wound healing |
| Bone cells | Osteoporosis |
| Retinal (eye) cells | Macular degeneration |
| Skeletal muscle cells | Muscular dystrophy |

The combination of a bioreactor attached to an in vivo plasmapheresis device exhibits a clear advantage over current techniques. The in vivo plasmapheresis device provides the bioreactor with a constant supply of culture media and a mechanism for cell generation in real time without removing blood from the patient. Additionally, the present invention will lower treatment costs for the patient and present an option for a less intrusive treatment regime. Furthermore, the present invention allows patients waiting for an organ donor the opportunity to grow their own new healthy organ. The present invention can be used to treat a number of human pathologies. The following are a small sample of the many useful applications of the present invention.

Burn victims may utilize the present invention to aid healing, repair, or function of the skin. Healthy dermal and epidermal cells can be taken from the patient and cultured inside a bioreactor to be later grafted back into the patient. Using the patient's own skin cells to culture skin grafts ensures a successful implantation with respect to host vs. graft disease. Additionally, if the patient is unable to support a bioreactor, due to illness or other factors, new skin tissue may be cultured in an allogenic or xenogenic bioreactor and transplanted to the patient.

Patients afflicted with chronic heart disease, including heart attacks and congestive heart failure, may utilize the present invention to ameliorate coronary conditions. Healthy heart muscle cells, derived from pluripotent stem cells, can be cultured inside a bioreactor to be later transplanted into the patient's failing heart to augment heart function. Additionally, if the patient is unable to support a bioreactor, due to illness or other factors, new heart muscle cells may be cultured in a allogenic or xenogenic bioreactor and transplanted to the patient.

Patients afflicted with various neural disorders, including Parkinson's disease, Alzheimer's disease, multiple sclerosis, spinal cord injuries, and strokes, may utilize the present invention to ameliorate neural disorders and conditions. Healthy neural cells, derived from pluripotent stem cells, can be cultured inside a bioreactor to be later transplanted into the patient in an appropriate location, dependent on the particular patient's condition. New neural cells will augment the function of the targeted tissue or organ. Additionally, if the patient is unable to support an in vivo bioreactor, due to illness or other factors, new neural cells may be cultured in an allogenic or xenogenic bioreactor and transplanted to the patient.

Patients afflicted with skeletal muscular disorders, including muscular dystrophy, may utilize the present invention to ameliorate skeletal muscular disorders and conditions. Healthy skeletal muscle cells, derived from pluripotent stem cells can be cultured inside a bioreactor to be later transplanted into the patient in an appropriate location, dependent on the needs of the particular patient. New skeletal muscle cells will augment the function of the targeted muscle. Additionally, if the patient if unable to support a bioreactor, due to illness or other factors, new skeletal muscle cells may be cultured in an allogenic or xenogenic bioreactor and transplanted to the patient.

Patients afflicted with disorders of the blood, including cancer, immunodeficiencies, inherited blood diseases, and leukemia, may utilize the present invention to ameliorate blood disorders. Healthy blood cells, derived from pluripotent stem cells, can be cultured inside a bioreactor to be later transplanted, or alternatively, discharged from the bioreactor. New blood cells will ameliorate the patient's condition. Additionally, if the patient is unable to support a bioreactor, due to illness or other factors, new blood cells may be cultured in an allogenic or xenogenic bioreactor for transfusion to the patient.

Patients subjected to high-dose chemotherapy (HDC) treatment for various disorders, including different types of cancer, may use the present invention to rebuild their immune system following HDC treatment where such therapy disables their immune system. Healthy autologous stem cells can be isolated from the patient prior to chemotherapy treatment, cryogenically frozen, and placed inside the bioreactor. Upon completion of the chemotherapy treatment, the stem cells can be unfrozen and systematically reintroduced into the patient to restore immune function.

Patients infected with human immunodeficiency virus (HIV) may utilize the present invention to promote helper T cell generation (CD4+). Healthy T lymphocytes may be isolated from the patient and placed inside the bioreactor. As the T lymphocytes proliferate they produce the cytokine Interleukin-2. Interleukin-2 enters the blood stream signaling CD4+ cells to become active and reproduce, thus offsetting the effect of HIV which attacks CD4+ cells.

Patients suffering from Type 1 diabetes may use the present invention to ameliorate their condition. Healthy islet cells, which produce insulin, can be placed inside an in vivo bioreactor. Insulin can be redirected to the patient's blood vessel through the catheter. Insulin produced by the healthy islet cells mimics the functionality of a healthy pancreas and mitigates the need for insulin injections.

Patients suffering from total or near total liver failure due to chronic hepatitis B may utilize the present invention to grow a new, healthy liver rather than use a donor organ. Pluripotent cells may be placed inside a specialized bioreactor and cultured to form a new liver. The liver can be later transplanted into the patient thus ameliorating symptoms associated with liver failure. Additionally, if the patient is unable to support a bioreactor, due to illness or other factors, a new liver can be cultured in an allogenic or xenogenic bioreactor and transplanted to the patient.

Patients needing organs of any type may use the present invention to grow a new, healthy organ rather than use a donor organ. Pluripotent cells may be placed inside a specialized bioreactor and stimulated to produce the appropriate organ. The organ can be later transplanted into the patient thus ameliorating a host of diseases and conditions. Additionally, if the patient is unable to support a bioreactor, due to illness or other factors, a new organ can be cultured in an allogenic or xenogenic bioreactor and transplanted to the patient.

Patients with genetic diseases, such as severe combined immunodeficiency (SCID), may utilize the present invention in combination with gene therapies, well known to those with ordinary skill in the art, to ameliorate genetic conditions. Cells isolated from the patient's core blood, or other stem cells, can be genetically modified to create healthy, wild type cells. These modified, healthy cells can be placed inside a bioreactor and released into the body as a therapeutic at strategic times throughout the patient's life to ameliorate the disorder.

While the present invention has been described in some detail for purposes of clarity and understanding, one skilled in the art will appreciate that various changes in form and detail can be made without departing from the true scope of the invention. All references referred to above are hereby incorporated by reference.

What is claimed is:

1. A method of treating cells, tissues or organs comprising:
   implanting an in vivo plasma separation device within a blood vessel of a patient or donor;
   separating blood plasma from whole blood in vivo using said plasma separation device;
   directing said plasma from the plasma separation device to a bioreactor; and
   exposing said plasma to cells, tissue or organ in said bioreactor.

2. A method of claim 1 including directing the exposed plasma from said bioreactor to the patient or donor.

3. A method of claim 1 or 2 including monitoring levels of one or more dissolved gaseous components in said blood plasma between the patient or donor and said bioreactor.

4. A method of claim 3 including supplying one or more gases to said blood plasma in response to monitored gaseous component levels.

5. A method of claim 1 or 2 including directing the exposed plasma from the bioreactor to the capillary bed of a tissue structure or organ of the patient or donor.

6. A method of claim 1 or 2 including transplanting the treated cells, tissue or organ into the patient or donor.

7. A method of claim 6 wherein said plasma separation device comprises a plasmapheresis filter element secured on or adjacent to an end of a multiple lumen catheter having a first and a second lumen, said filter element comprising a hollow fiber and/or sheet membrane having a pore size capable of separating blood plasma and selected blood components from whole blood, passing said blood plasma and selected components through said membrane and directing said plasma and selected components through the first lumen of said catheter to said bioreactor.

8. A method of claim 1 or 2 comprising exposing a patient's own cells, tissue or organ to autologous plasma in said bioreactor.

9. A method of claim 8 wherein said plasma separation device comprises a plasmapheresis filter element secured on or adjacent to an end of a multiple lumen catheter having a first and a second lumen, said filter element comprising a hollow fiber and/or sheet membrane having a pore size capable of separating blood plasma and selected blood components from whole blood, passing said blood plasma and selected components through said membrane and directing said plasma and selected components through the first lumen of said catheter to said bioreactor.

10. A method of claim 8 including transplanting the patient's treated cells, tissue or organ into the patient.

11. A method of claim 10 including returning said exposed autologous plasma to the patient.

12. A method of claim 10 wherein said plasma separation device comprises a plasmapheresis filter element secured on or adjacent to an end of a multiple lumen catheter having a first and a second lumen, said filter element comprising a hollow fiber and/or sheet membrane having a pore size capable of separating blood plasma and selected blood components from whole blood, passing said blood plasma and selected components through said membrane and directing said plasma and selected components through the first lumen of said catheter to said bioreactor.

13. A method of claim 8 including returning said exposed autologous plasma to the patient.

14. A method of claim 1 or 2 comprising directing allogenic or xenogenic plasma from a donor to a bioreactor containing a patient's cells, tissue or organ, passing the allogenic or xenogenic plasma through an immune isolation membrane and thereafter exposing the plasma to cells, tissue or organ, and directing the exposed plasma to a patient or donor.

15. A method of claim 14 including transplanting exposed cells, tissue or organ to a patient or donor.

16. A method of claim 14 wherein said plasma separation device comprises a plasmapheresis filter element secured on or adjacent to an end of a multiple lumen catheter having a first and a second lumen, said filter element comprising a hollow fiber and/or sheet membrane having a pore size capable of separating blood plasma and selected blood components from whole blood, passing said blood plasma and selected components through said membrane and directing said plasma and selected components through the first lumen of said catheter to said bioreactor.

17. A method of claim 1 or 2 wherein said plasma separation device comprises a plasmapheresis filter element secured on or adjacent to an end of a multiple lumen catheter having a first and a second lumen, said filter element comprising a hollow fiber and/or sheet membrane having a pore size capable of separating blood plasma and selected blood components from whole blood, passing said blood plasma and selected components through said hollow fiber and/or sheet membrane and directing said plasma and selected components through the first lumen of said catheter to said bioreactor.

18. A method of claim 17 including directing the exposed plasma from said bioreactor to a blood vessel of the patient or donor through the second lumen of said catheter.

19. A method of claim 17 including providing a cell culture bed in said bioreactor and passing said plasma through said cell culture bed, and exposing said plasma to substantially all cells in the cell culture bed.

20. A method of claim 17 including supplementing the plasma with one or more supplement compositions in said bioreactor.

21. A method of claim 17, treating the exposed plasma from the bioreactor to remove selected toxins or components thereof and thereafter directing the plasma to the patient or donor.

22. An apparatus for carrying out a method of treating cells, tissues or organs comprising:
   a filter for being planted in a patient's blood vessel comprising a plurality of elongated hollow microporous fibers having an interior lumen and a fiber wall having a pore size capable of allowing plasma to diffuse therethrough, wherein said fibers comprise a fiber wall having a plurality of zones between the inner and outer wall surfaces, each of said zones having a mass density different than the mass density of an adjacent zone, said fiber wall characterized by having a lower mass density zone at the inner wall surface and a higher mass density zone at the outer wall surface;

a multiple lumen catheter in fluid communication with the interior fiber lumen including a first lumen for directing separated blood plasma from said fiber lumen and a second lumen for directing blood plasma to the patient;

a bioreactor; and a first conduit for directing plasma from the first lumen to said bioreactor, and a second conduit for directing exposed plasma from said bioreactor to the second lumen.

23. An apparatus of claim 22 wherein said membrane fiber wall has two mass density zones.

24. An apparatus of claim 22 wherein said membrane fiber wall has three mass density zones.

25. An apparatus of claim 22 wherein membrane fiber wall has four or more mass density zones.

26. An apparatus of claim 23, 24 or 25 wherein each of said zones is characterized by a different average nominal pore size.

27. An apparatus of claim 26 wherein the fiber wall structure comprises a continuous change in mass density from the outer wall surface to the inner wall surface.

28. An apparatus of claim 26 wherein said lower mass density zone is characterized by a nominal average pore diameter of between about 1 $\mu$m and about 60 $\mu$m.

29. An apparatus of claim 28 wherein said higher mass density zone is characterized by a nominal average pore diameter of between about 0.3 $\mu$m and about 1 $\mu$m.

30. An apparatus of claim 26 wherein said higher mass density zone is characterized by a nominal average pore diameter of between about 0.3 $\mu$m and about 1 $\mu$m.

31. An apparatus of claim 22 characterized by having the capability of extracting at least 0.75 (ml/min)(cm$^2$×mm Hg) of blood plasma at trans-membrane pressures of between about 5 and about 20 mm Hg.

32. An apparatus of claim 22 wherein the fiber wall structure comprises a continuous change in mass density from the outer wall surface to the inner wall surface.

* * * * *